United States Patent [19]
Katz

[11] Patent Number: 5,490,596
[45] Date of Patent: Feb. 13, 1996

[54] AUTOCLAVE BAG

[76] Inventor: Jay Katz, 56627 Arch Ct., Elkhart, Ind. 46516

[21] Appl. No.: 370,326

[22] Filed: Jan. 10, 1995

[51] Int. Cl.⁶ ............................................. A61B 19/02
[52] U.S. Cl. ................. 206/439; 206/484.1; 383/109; 383/117
[58] Field of Search ................... 206/439, 484, 206/484.1, 438; 383/109, 117

[56] References Cited

U.S. PATENT DOCUMENTS

| | | | |
|---|---|---|---|
| 4,041,203 | 8/1977 | Brock et al. | 206/439 X |
| 4,042,170 | 8/1977 | Ekman et al. | 206/439 X |
| 4,205,611 | 6/1980 | Slawinski | 383/117 X |
| 4,228,834 | 10/1980 | Desnick | 383/117 X |
| 4,380,485 | 4/1983 | Schuster | 206/439 X |

*Primary Examiner*—Bryon P. Gehman
*Attorney, Agent, or Firm*—Watson, Cole, Grindle & Watson

[57] ABSTRACT

An autoclave bag having an outer ply of mesh fabric with interstices formed throughout the mesh, an inner ply of a film of synthetic polymer, and an intermediate, adhesive ply bonding the outer and inner plies and entering the interstices of the outer ply.

10 Claims, 1 Drawing Sheet

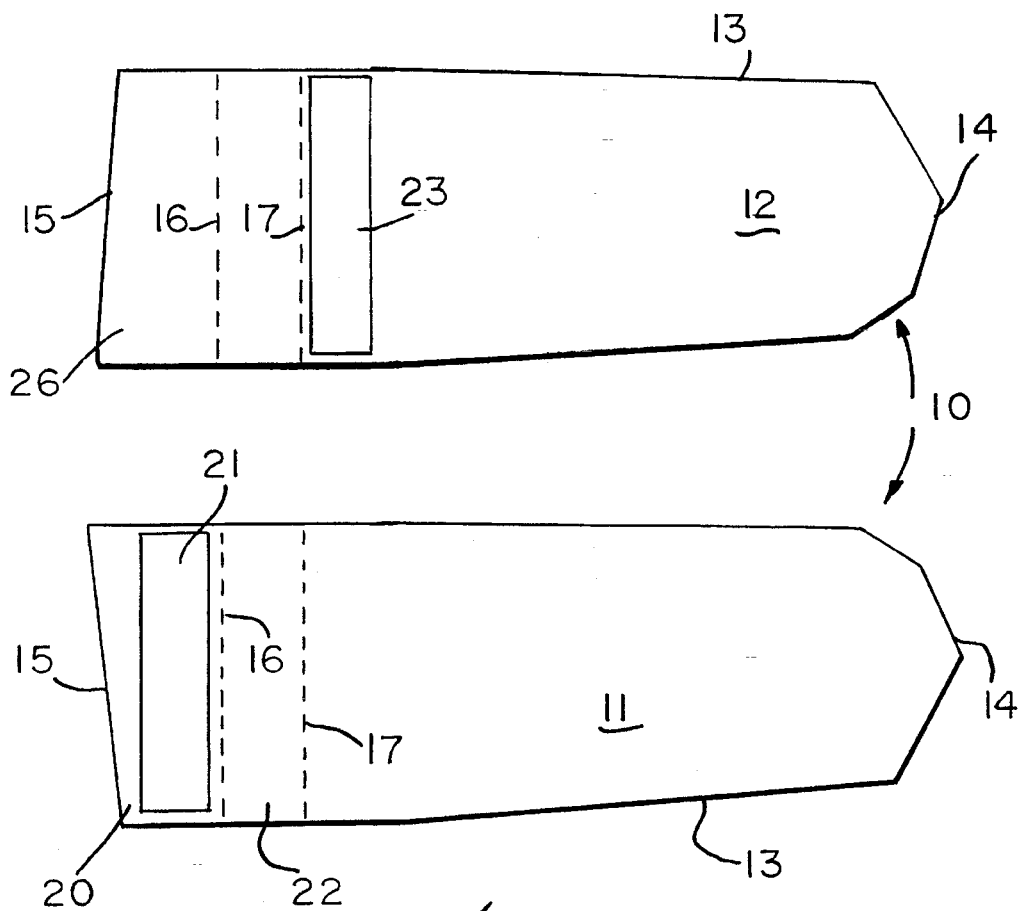
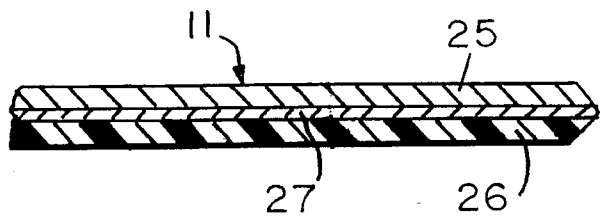

AUTOCLAVE BAG

BACKGROUND OF THE INVENTION

The present invention relates generally to containers that are specifically adapted to hold materials to be sterilized by being subjected to heat. More specifically, it relates to bags that are subjected to autoclaving temperatures and pressures and are specifically designed to hold surgical or dental instruments.

Particularly in view of the recognition that viruses and bacteria, such as the HIV virus, may be transferred from a medical care provider to a patient, or vice-versa, it is commonplace to sterilize medical and dental instruments before they are to be used. Thus, a variety of bags have been designed in order to contain surgical and dental instruments, after which the bags are subjected to high temperatures in a heat chamber. That chamber is referred to hereinafter as an autoclave, although there may be definitions of that term which are not precisely met, e.g., the heating chamber may not be at superatmospheric pressure.

Autoclave bags must have several features which are necessary in order to have them function effectively, and other features that are highly desirable from the standpoint of economy. For example, an autoclave bag must have sufficient strength to resist ripping or tearing in use. Associated therewith is the property that it must be puncture-resistant, specifically where it is to hold surgical instruments, such as scalpels or other pointed devices. Yet any bag that holds surgical instruments is subject to being punctured when the bag is removed from the autoclave and, of necessity, instruments inside the bags shift. Such shifting makes the bag subject to being ripped or torn by the weight and movement of the medical instruments within the bag. When a bag tears, and the medical instrument comes into contact with surrounding surfaces, there is a concomitant loss of sterility of that instrument. Should the tearing take place to such an extent that the instruments fall from the bag, the instruments may well be damaged and, of course, their loss of sterility would be assured.

Many existing autoclave bags have to be ripped open for a person to gain access to the instruments therein. Such ripping often causes the instruments to scatter on trays because the force necessary to open such a bag is considerable, and such scattering contributes to loss of sterility. Also, many autoclave bags presently in use will still be wet when the autoclave is opened at ambient, atmospheric pressure. The only way to avoid the bag still being wet is if it goes through a drying cycle, which is often omitted because the person handling the autoclave wishes to retrieve the instruments for immediate use. If there is a paper backing on the autoclave bag and a door to the autoclave is opened while that backing is wet, the instruments therein will no longer be sterile. This is also the case if the paper backing becomes wet or acquires moisture from any source subsequent to autoclaving.

In addition to the need for a puncture-resistant, strong auto-clave bag, it is also highly desirable that an autoclave bag be reusable. Obviously, those autoclave bags that are opened by ripping or tearing are subject to use only once. Yet there is an environmental objective in having bags be reusable for perhaps one hundred times, thereby requiring less plastic waste to go into land fills.

Still another feature that is important in an autoclave bag is flexibility. If the bag or other container for surgical instruments is rigid, there is an increased possibility that shifting of the surgical instruments within the container will increase the likelihood that rigid walls will be punctured by a sharp instrument. Yet the bag wall must have sufficient strength so that it will be enable to resist puncture and yet be flexible. Thus, it is a goal to have an autoclave bag that has all the requisite features that will enable the bag to be maintained in use without the disadvantages inherent in the prior art.

It is, accordingly, a primary object of the present invention to provide an autoclave bag that is reusable, puncture-resistant and of such inherent strength that it does not rip or tear in use, yet is flexible. Surgical instruments may be placed within such a bag and the bag subjected to high autoclaving temperatures and pressures. After removal of the bag from the autoclave, the surgical instruments can be readily removed from the bag without contamination, and the bag can then be reused to subject another batch of surgical instruments to autoclaving conditions.

SUMMARY OF THE INVENTION

In its basic concept my invention of a reusable, flexible bag for holding surgical and/or dental instruments to be subjected to autoclaving conditions is comprised of a three-ply bag. The outer ply is in the form of a mesh fabric made from a synthetic polymeric material. The mesh is not continuous but has interstices formed throughout its area. An inner ply is provided, which is in the form of a continuous film of flexible synthetic polymeric material resistant to the passage of moisture therethrough. There is also an intermediate ply in the form of an adhesive layer having high sheer strength, long-term holding power, and resistance to liquefaction under autoclaving conditions. The intermediate ply bonds the outer and inner plies together and augments its bonding by entering the interstices of the mesh of the outer ply. By such coaction between the intermediate, adhesive ply and the mesh fabric, surgical instruments placed within the bag may be auto-claved without puncture of the bag or subjecting the contents of the bag to loss of sterility by exposure to moisture after the autoclaving has been completed.

In preferred embodiments of my invention, the outer ply may be formed from a nylon fabric mesh and the inner ply from a transparent film of polyvinyl chloride resin. When such a bag is held up to a light source, the outline of its contents is discernible to the unaided eye because of the passage of light through the interstices of the mesh, the intermediate, transparent or translucent adhesive, and the transparent inner film, thus providing some identification of the contents of the bag.

Since the bag must be maintained in closed position during autoclaving, the bag is preferably in an elongated form completely closed except for one open end through which surgical or like instruments may be inserted and removed. Closure means is located on that bag end to seal the bag against ingress of moisture while it is being subjected to autoclaving temperatures. More preferably, the elongated bag end is foldable on itself and, after folding, will be held in closed position. One preferred closure means include male and female hook-and-loop strips, often marketed under the trademark VELCRO, that coact to releasably hold the bag in closed position, one of such hook-and loop strips being held on the obverse and another on the reverse of substantially parallel bag surfaces so that, after folding, the male and female Velcro surfaces coact to hold the bag closed, yet provide easy ingress to the contents of the bag after autoclaving by simply separating the hook-and loop.

These and other objects, features, and advantages of my autoclave bag will become more apparent when considered in connection with the drawings of a preferred embodiment thereof, in which:

FIG. 1 is a bottom plan view of the bag;

FIG. 2 is a top plan view of the bag, and

FIG. 3 is a highly enlarged, diagrammatic sectional view of one layer of the bag, showing the structure of the plies therein.

DETAILED DESCRIPTION OF THE BEST MODE

Referring now to the drawings, and to FIGS. 1 and 2 in particular, a best mode of the bag 10 is shown as an oblong, elongated sock of material having generally opposed top surface 11 and bottom surface 12 stitched together at their peripheries 13 in any convenient manner. It will be apparent that such means for holding the upper and lower bag elements 11 and 12 together can include any means of stitching or joinder that is convenient and which will hold the elements together, usually with an overlap of material. Thus, an excess of material may be tucked under the periphery 13 and stitched over such tuck so that the resultant bag is water tight along the lines of joinder of the upper and lower surfaces or layers.

The autoclave bag 10 terminates at one end, which is the right end as shown in FIGS. 1 and 2 in a closed foot 14, and at its other end, shown to the left in those figures, in an open end 15. The bag end 15 is adapted to be folded along first and second fold lines 16 and 17, indicated by broken lines in the two figures. In accordance with my presently intentioned best mode, such folds will take place inwardly, i.e., in the direction of what has been labeled as the lower surface 12 of the bag. Attached firmly by adhesive or other means to the first, outer fold portion 20 of the bag is a strip 21 of hook-type, hook-and-loop fabric, often marketed under the trademark VELCRO. The second, inner fold portion of the bag 22, which is located inwardly of the first fold portion 20, has no hook-and loop fastening means affixed thereto. However, immediately inwardly of the second fold line 17 is a second loop strip 23, which is a female portion adapted to cooperate with the hook-type strip in a manner that is well known in the art.

From this description it will be apparent as seen in FIGS. 1 and 2 the bag is in open position so that surgical instruments may be inserted into and removed from the bag through the open end 15. When it is desired to close the bag, outer fold portion 20 is folded along fold line 16 to a position where it overlies, but of course does not adhere to second fold portion 22. First fold portion 20 is folded along fold line 16 in such a manner that, as seen in FIG. 2, the first fold will underlie second fold portion 22 of the bag, so that in FIG. 2 the outer fold portion carrying the Velcro strip 21 will not be seen. As so folded in FIG. 1, the first fold portion 20 will overlie second fold portion 22, with and hook-and-loop strip 21 being exposed. Thereafter, a second fold along fold line 17 will bring hook-and loop strip 21 into contact with hook-and loop strip 23. Because the hook-and loop strips are of opposite types, strip 21 being designated as the male, i.e., hook-type member from which appendages protrude, and strip 23 being a female, i.e., loop-type member adapted to receive such appendages, upon such folding the formerly open end 15 of the bag will be closed and, because of the two folds, will seal the instruments that lie within the bag from ambient moisture.

The structure of various plies of the bag is best seen in FIG. 3, which is greatly enlarged for the purpose of illustration. As seen in FIG. 3, the top surface 11 and bottom surface 12 of autoclave bag 10 are formed with an outer ply 25 of nylon mesh. There is an innermost ply 26 formed from polyvinyl chloride resin. Between the two and designated by reference numeral 27, is an intermediate, adhesive ply. The adhesion of the outer and inner plies 25 and 26 to each other is greatly enhanced by the intermediation of adhesive layer 27 because of the mesh structure of the outer ply. Any such mesh, typified by a woven or knitted fabric has interstices spaced throughout the mesh, and the adhesive layer 27, being tacky and somewhat flowable prior to setting, will at least in part enter such interstices and contact not only the bottom of the mesh layer but also sides of the strands from which the mesh is formed. Such area of contact is therefore greater, e.g., than the area of contact between adhesive layer 27 and inner layer 26, for that area of contact is solely planar.

With regard to the material from which the outer ply 25 is formed, the material must be obviously such as will be strongly resistant to decomposition or deterioration at autoclave temperatures and pressures. Synthetic polymeric materials in the form of a mesh according to this invention meet that requirement, and nylon appears to meet it most adequately, since it is inert and odorless and meets OSHA or WHMIS standards. With regard to the inner layer, which is in the form of a clear plastic film, that layer is formed from a continuous film of flexible synthetic polymeric material resistant to the passage of moisture therethrough or to inadvertent penetration by instruments contained within the bag. In my preferred embodiment polyvinyl chloride resin manufactured by Reynolds Metals Company under the trademark Reynolon, has been selected because it also meets OSHA or WHMIS standards, and in its physical state it is odorless and substantially transparent.

With regard to the adhesive layer, I presently prefer a high performance, acrylic, pressure sensitive adhesive, such as one sold under the trademark Morgan Adhesives by Mactac. The product description is IF2015. I have used an adhesive protected on both sides by a release-treated, polycoated Kraft paper liner. Such acrylic adhesive has excellent ultraviolet life stability and elevated temperature resistance. It provides aggressive tack and high sheer strength for bonding. The thickness should be at least five mils to permit contact not only on the bottom surfaces of the nylon mesh but, as stated, to permit contact on side surfaces of such mesh. Such adhesive is also resistant to water, detergent, alcohol, solubility, although it is not recommended for contact with solvent such as ketones, esters, and some chlorinated hydrocarbons. However, it is not contemplated that the surgical or dental instruments to be autoclaved will be contaminated with such materials. Even if they are, it is the PVC resin rather than the adhesive that will be in direct contact with such materials. The adhesive preferably has a temperature range of about −40° F. to 302° F. in use, which should make it sufficiently resistant to autoclaving temperatures. Other adhesives may well prove to be superior in use as resistant to decomposition or excess flowability at still higher temperatures.

With the materials that now constitute the best mode of the present invention, I have achieved an autoclave bag that is flexible, highly flame and heat resistant, and is translucent or transparent due to the mesh and the substantially transparent adhesive and PVC film used as the inner ply. The use of hook-and loop fasteners has also proved highly satisfactory since they, too, resist decomposition at high temperatures and, while effectively sealing the end of the bag, can easily be separated for removal of the instruments within the bag and then subsequent reuse of the bag. Indeed, the bag life is probably only limited by the life of the hook-and loop fasteners.

It will be apparent to those of skill in this art that various modifications and alterations may be made to the preferred embodiment of my invention with respect to which that invention has been described hereinbefore. As to all such alterations and modifications which would be obvious to those of such skill, it is desired that they be included within the purview of my invention, which is to be limited only by the scope, including equivalents, of the following, appended claims.

I claim:

1. A reusable, flexible bag for holding surgical instruments to be subjected to autoclaving temperatures, comprising:
   an outer ply in the form of a mesh fabric made of synthetic polymeric material and having interstices formed throughout the mesh,
   an inner ply in the form of a continuous film of flexible synthetic polymeric material resistant to the passage of moisture therethrough and to inadvertent penetration by instruments contained therewithin, and
   an intermediate ply in the form of an adhesive layer having high sheer strength, long-term holding power, and resistance to liquefaction at autoclaving temperatures, said intermediate ply bonding said outer and inner plies together and augmenting said bond by entering the interstices in the mesh of said outer ply, so that surgical instruments placed within said bag will be autoclaved without puncture of the bag or subjecting the contents of the bag to loss of sterility by exposure to moisture after said autoclaving has been completed.

2. An autoclave bag as claimed in claim 1, in which said outer ply is formed from mesh nylon fabric.

3. An autoclave bag as claimed in claim 1, in which said inner ply is transparent.

4. An autoclave bag as claimed in claim 3, in which said inner ply is formed from polyvinyl chloride resin.

5. An autoclave bag as claimed in claim 3, in which the contents of said bag can be discerned by holding said bag against a light source, said contents being discernible through the interstices in said outer layer mesh, said adhesive layer and said transparent inner ply.

6. A reusable, flexible, elongated bag for the insertion and removal of surgical instruments through an open end thereof, said bag and said instrument being subjected to autoclaving temperatures, comprising
   an outer ply in the form of a mesh fabric made of synthetic polymeric material and having interstices formed throughout the mesh,
   an inner ply in the form of a continuous film of flexible synthetic polymeric material resistant to the passage of moisture therethrough and to inadvertent penetration by instruments contained therewithin;
   an intermediate ply in the form of an adhesive layer having high sheer strength, long-term holding power, and resistance to liquefaction at autoclaving temperatures, said intermediate ply bonding said outer and inner plies together and augmenting said bond by entering the interstices in the mesh of said outer ply, so that surgical instruments placed within said bag will be autoclaved without puncture of the bag or subjecting the contents of the bag to loss of sterility by exposure to moisture after said autoclaving has been completed, and
   closure means located at said open bag end so that said bag can be sealed against ingress of moisture while it is subjected to autoclaving temperatures.

7. An autoclave bag as claimed in claim 6, in which said elongated bag end is foldable on itself and said closure means holds said bag in folded, closed position.

8. An autoclave bag as claimed in claim 7, in which said bag end is folded on itself twice and held in such position by said closure means.

9. An autoclave bag as claimed in claim 8, in which said closure means includes male and female hook-and loop strips that coact to releasably hold said bag in closed position.

10. An autoclave bag as claimed in claim 6, in which said closure means includes male and female hook-and loop strips that coact to releasably hold said bag in closed position.

* * * * *